United States Patent [19]
Wascher et al.

[11] Patent Number: 6,007,476
[45] Date of Patent: Dec. 28, 1999

[54] NON-PARTICLE, NON-PHOTONIC DEVICE AND METHOD FOR AFFECTING ANGIOGENESIS

[75] Inventors: Rick R. Wascher, Rock Island; C. Douglas Williams, Signal Mountain; Floyd E. Bouldin, Murfreesboro, all of Tenn.

[73] Assignee: EMF Therapeutics, Inc., Chattanooga, Tenn.

[21] Appl. No.: 08/955,604

[22] Filed: Oct. 22, 1997

[51] Int. Cl.⁶ .............................. A61B 17/52; A61N 1/00
[52] U.S. Cl. .................................... 600/9; 600/13; 600/14
[58] Field of Search .................................... 600/13, 14, 9

[56] References Cited

U.S. PATENT DOCUMENTS

| | | |
|---|---|---|
| 96,044 | 10/1869 | Smith . |
| 703,989 | 7/1902 | Burry . |
| 770,433 | 9/1904 | Kinraide . |
| 781,448 | 1/1905 | McIntyre . |
| 2,102,790 | 12/1937 | Drollinger . |
| 3,570,476 | 3/1971 | Gregg ............................................. 601/2 |
| 3,890,953 | 6/1975 | Kraus et al. ................................. 600/14 |
| 3,915,151 | 10/1975 | Kraus ........................................... 600/13 |
| 4,066,065 | 1/1978 | Kraus ........................................... 600/13 |
| 4,134,395 | 1/1979 | Davis ........................................ 600/407 |
| 4,233,965 | 11/1980 | Fairbanks ................................... 600/14 |
| 4,303,636 | 12/1981 | Gordon ..................................... 424/1.29 |
| 4,402,309 | 9/1983 | Harrison .................................... 600/10 |

(List continued on next page.)

FOREIGN PATENT DOCUMENTS

| | | |
|---|---|---|
| 0 371 504 | 6/1990 | European Pat. Off. . |
| 196 00 744 | 7/1997 | Germany . |

OTHER PUBLICATIONS

Chemical Abstracts, vol. 128, No. 14 6 Apr. 1998, Ikeda, Shigeki et al.; "Enhancement of the effect of an angiogenesis inhibitor on murine tumors by hypothermia".

Chemical Abstracts, vol. 124, No. 3, 15 Jan. 1996, Robins, H. Ian et al.; "Cytokine induction by 41.8 degree C whole body hyperthermia".

Bone, vol. 19, No. 1 Supplement, Jul. 1996, pp. 39S–57S, by H. Winet, "The Role of Microvasculature in Normal and Perturbed Bone Healing as Revealed by Intravital Microscopy".

Proceeding Abstract of the 4th EBEA Congress, Zagreb, Croatia, Nov. 19–21, 1998; G. Sersa et al., "Tumour Blood Flow Changes Induced by Application of Electric Pulses".

Abstract and Article: Journal of Cellular Physiology 134:37–45 (1988); Yen–Patton, et al., "Endothelial Cell Response to Pulsed Electromagnetic Fields: Stimulation of Growth Rate and Angiogenesis in Vitro".

Guterl, Fred; "Beauty and Magnets"; Discover Magazine, Mar. 1997 pp. 38–43.

O'Brien, Jim; "Revolutionary New Magnetic Therapy Kos Arthritis Pain", Your Health Magazine, Apr. 6, 1993, pp. 17–18.

*Primary Examiner*—Cary O'Connor
*Assistant Examiner*—Navin Natnithithadha
*Attorney, Agent, or Firm*—Rick R. Wascher

[57] ABSTRACT

A method and apparatus for affecting angiogenesis in biological subjects such as mammals. The method employs the use of an apparatus which is capable of producing a magnetic field of a particular nature which has been proven in animal studies to affect angiogenesis. The apparatus includes a frame, a plurality of magnets capable of producing a magnetic field wherein each of the plurality of magnets has a north pole and a south pole and a longitudinal axis passing therethrough and are partially held in place by the frame. A coil of electrically conducting material is wrapped about the plurality of magnets in an orthogonal relationship to the longitudinal axis of each of the plurality of magnets. A source of electrical energy supplies an electrical current to the coil enabling a magnetic field to be produced therefrom. A switch is provided to enable the electrical current to flow in a first direction and optionally in a second direction opposite to the first direction. A rectifier is provided to alter the inherent supply voltage (e.g., 60 hertz) to a 120 hertz half sine or corresponding DC square wave form.

49 Claims, 9 Drawing Sheets

U.S. PATENT DOCUMENTS

| | | | |
|---|---|---|---|
| 4,622,952 | 11/1986 | Gordon | 600/10 |
| 4,626,792 | 12/1986 | Liboff et al. | 359/342 |
| 4,765,310 | 8/1988 | Deagle et al. | 600/14 |
| 4,818,697 | 4/1989 | Liboff et al. | 435/173.5 |
| 4,838,850 | 6/1989 | Rosengart | 600/14 |
| 4,932,951 | 6/1990 | Liboff et al. | 600/13 |
| 5,014,699 | 5/1991 | Pollack et al. | 607/2 |
| 5,045,050 | 9/1991 | Liboff et al. | 600/9 |
| 5,059,298 | 10/1991 | Liboff et al. | 204/628 |
| 5,067,940 | 11/1991 | Liboff et al. | 600/13 |
| 5,077,934 | 1/1992 | Liboff et al. | 47/1.3 |
| 5,084,003 | 1/1992 | Susic | 600/13 |
| 5,087,336 | 2/1992 | Liboff et al. | 600/14 |
| 5,088,976 | 2/1992 | Liboff et al. | 600/13 |
| 5,090,423 | 2/1992 | Matsuda et al. | 607/154 |
| 5,100,373 | 3/1992 | Liboff et al. | 600/13 |
| 5,106,361 | 4/1992 | Liboff et al. | 600/13 |
| 5,123,898 | 6/1992 | Liboff et al. | 600/13 |
| 5,131,904 | 7/1992 | Markoll | 600/14 |
| 5,143,588 | 9/1992 | Liboff et al. | 204/155 |
| 5,160,591 | 11/1992 | Liboff et al. | 204/155 |
| 5,183,456 | 2/1993 | Liboff et al. | 600/9 |
| 5,195,940 | 3/1993 | Baylink | 600/14 |
| 5,211,622 | 5/1993 | Liboff et al. | 600/9 |
| 5,215,633 | 6/1993 | Liboff et al. | 204/155 |
| 5,215,642 | 6/1993 | Liboff et al. | 435/286.1 |
| 5,224,922 | 7/1993 | Kurtz | 600/13 |
| 5,267,939 | 12/1993 | Liboff et al. | 600/13 |
| 5,269,745 | 12/1993 | Liboff et al. | 600/13 |
| 5,269,746 | 12/1993 | Jacobson | 600/13 |
| 5,290,409 | 3/1994 | Liboff et al. | 204/155 |
| 5,312,321 | 5/1994 | Holcomb | 600/9 |
| 5,312,534 | 5/1994 | Liboff et al. | 435/285.2 |
| 5,318,561 | 6/1994 | McLeod et al. | 600/14 |
| 5,330,410 | 7/1994 | Baylink | 600/13 |
| 5,344,384 | 9/1994 | Ostrow et al. | 600/13 |
| 5,366,435 | 11/1994 | Jacobson | 600/13 |
| 5,368,544 | 11/1994 | Tran et al. | 600/9 |
| 5,387,176 | 2/1995 | Markoll | 600/14 |
| 5,437,600 | 8/1995 | Liboff et al. | 600/9 |
| 5,441,495 | 8/1995 | Liboff et al. | 600/9 |
| 5,453,073 | 9/1995 | Markoll | 600/14 |
| 5,458,558 | 10/1995 | Liboff et al. | 600/13 |
| 5,518,495 | 5/1996 | Kolt | 600/13 |
| 5,518,496 | 5/1996 | McLeod et al. | 600/14 |
| 5,658,234 | 8/1997 | Dunlavy | 600/9 |
| 5,665,049 | 9/1997 | Markoll | 660/14 |
| 5,669,868 | 9/1997 | Markoll | 600/14 |

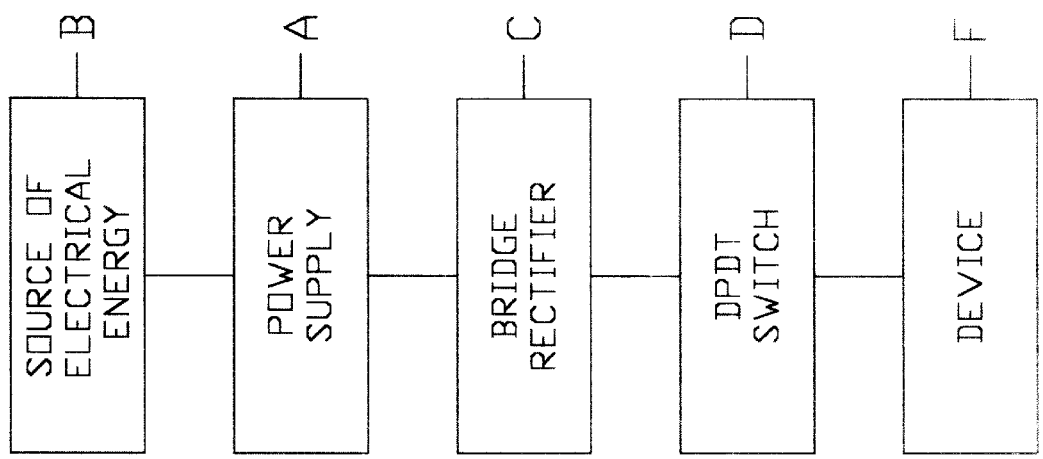

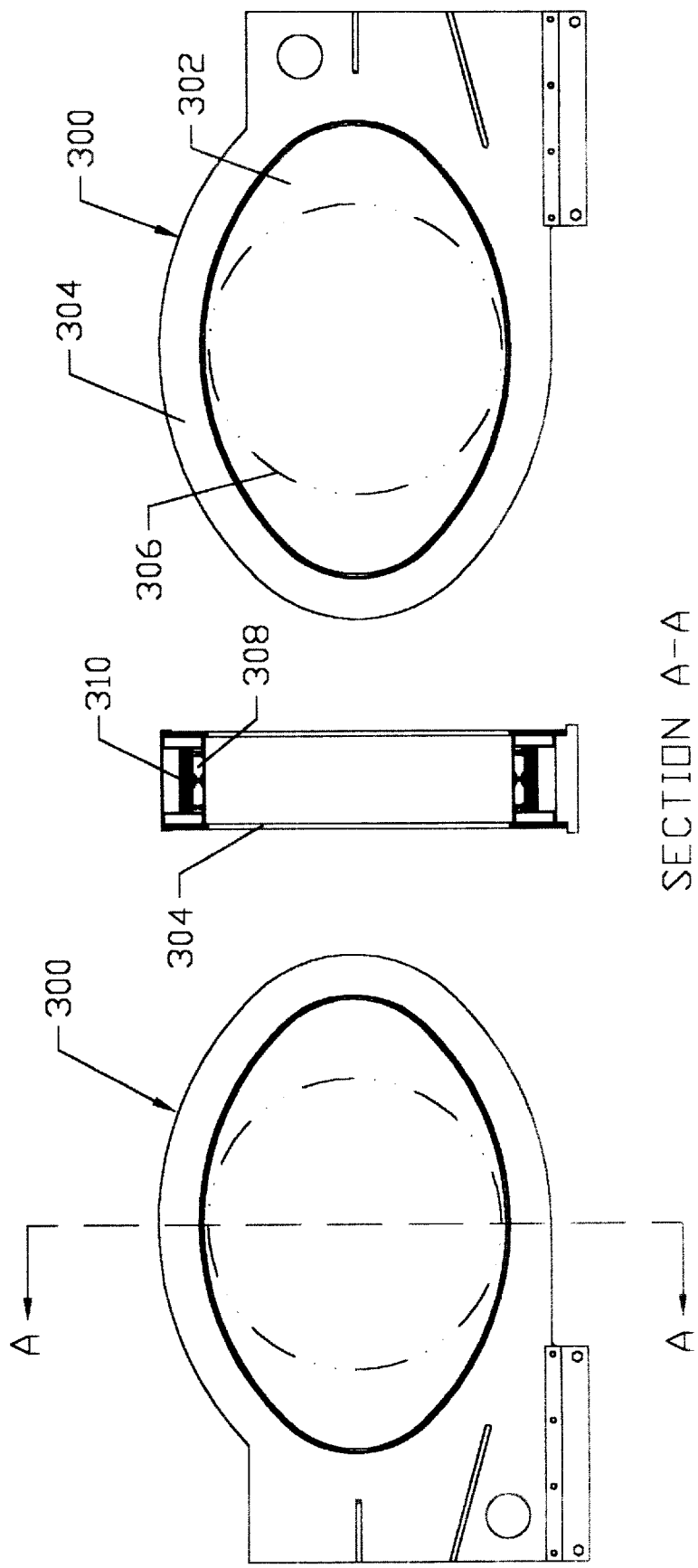

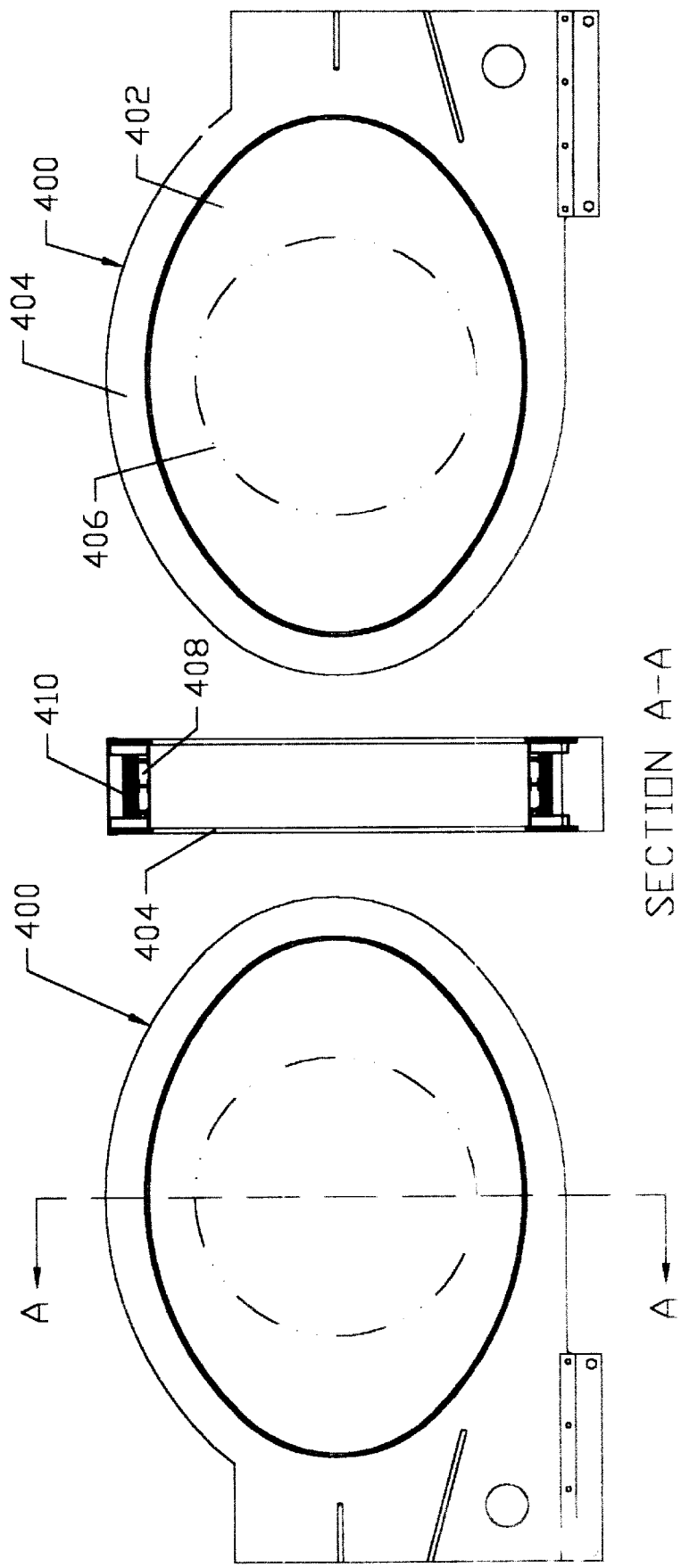

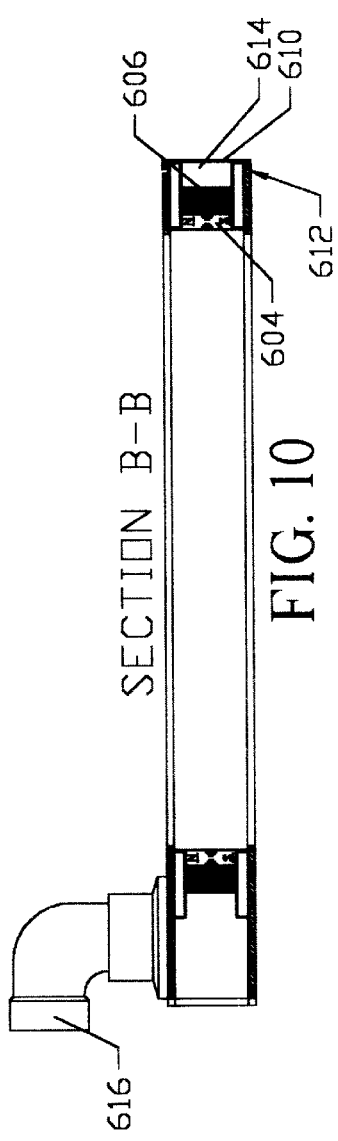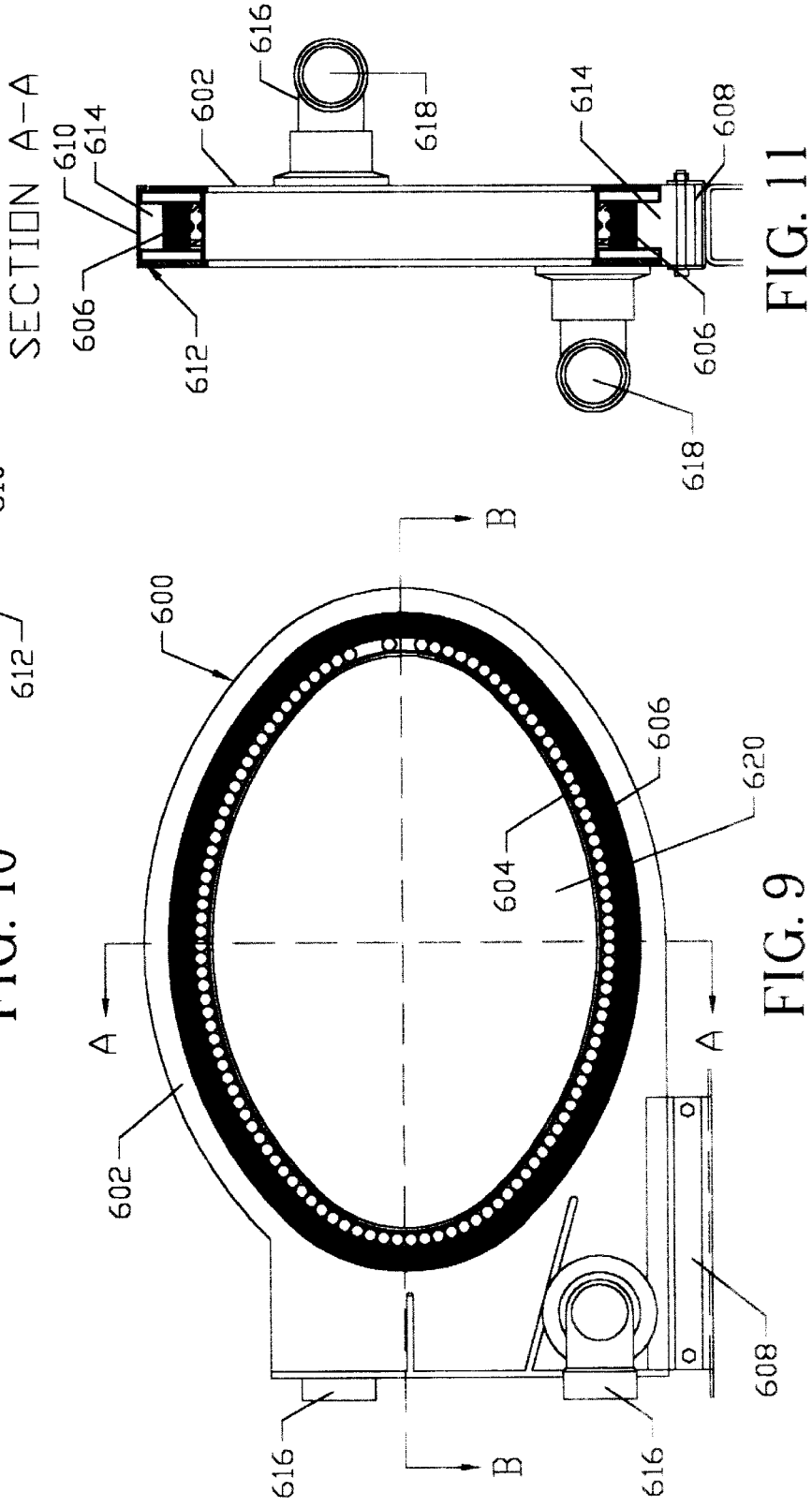

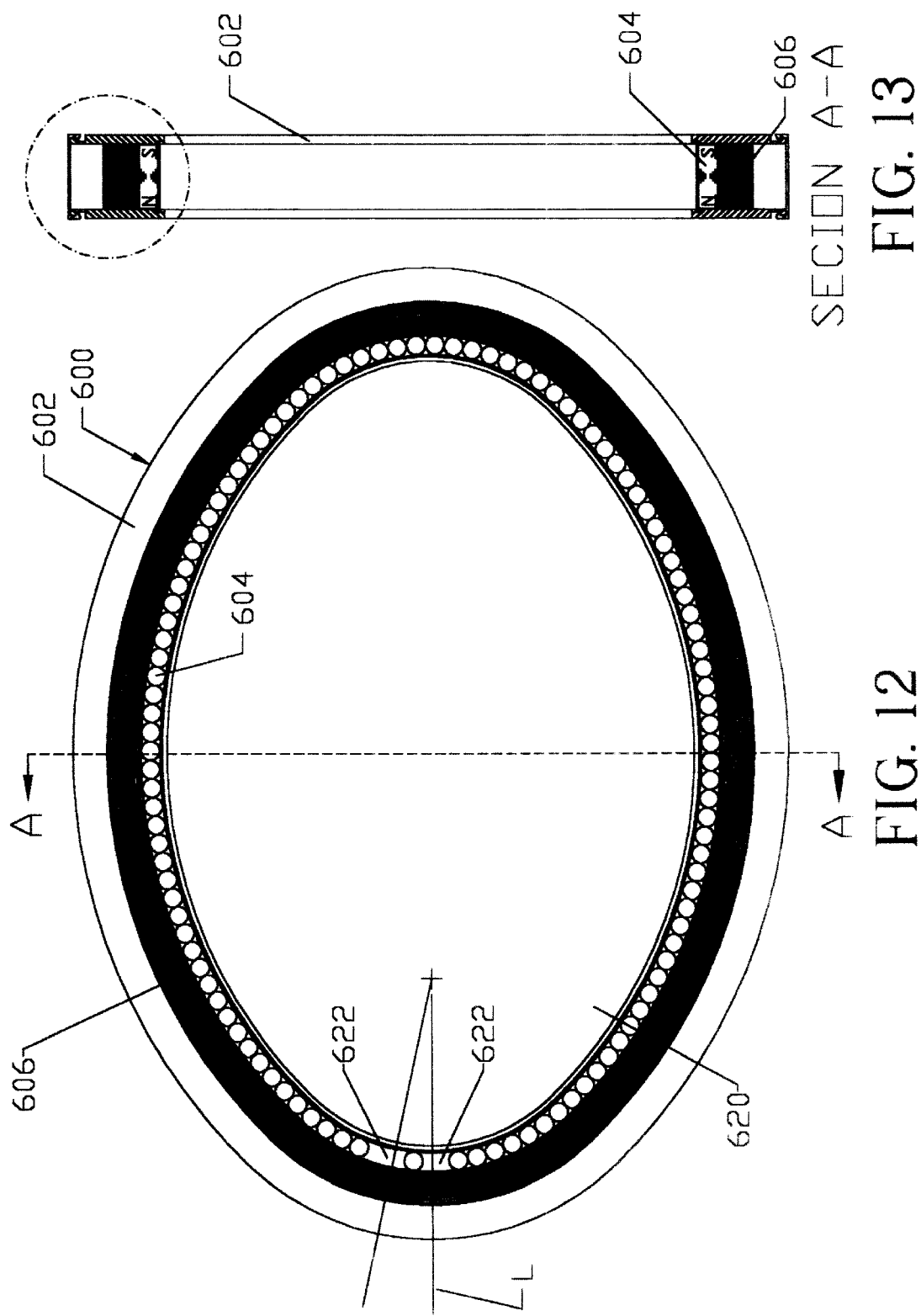

NON-PARTICLE, NON-PHOTONIC DEVICE AND METHOD FOR AFFECTING ANGIOGENESIS

BACKGROUND OF THE INVENTION

1. Field of the Invention

"Angiogenesis" may be defined as the formation or the initiation of the growth of blood carrying vessels or capillaries in a biological subject, particularly mammals.

The present inventive discovery is directed to the use of a device capable of producing a magnetic field or flux field (e.g., a magnetic or electric field). The inventive discovery presented herein uses a magnetic or flux field which has been determined to be capable of affecting the rate of angiogenic activity in biological subjects such as mammals.

It is believed that the present inventive discovery was universally unknown to mankind prior to the time it became known the inventors hereof

2. Description of the Related Art

In mature (non-growing) capillaries the vessel wall is composed of an endothelial cell lining, a basement membrane and a layer of cells called pericytes which partially surround the endothelium. The pericytes are contained within the same basement membrane as the endothelial cells and occasionally make direct contact with them. (See Background FIG. A).

With reference to Background FIG. B, angiogenic factors (the black triangles) bind to endothelial cell receptors and initiate the sequence of angiogenesis. When the endothelial cells are stimulated to grow, they secrete proteases which digest the basement membrane surrounding the vessel. The junctions between endothelial cells are altered, cell projections pass through the space created and the newly formed sprout grows towards the source of the stimulus.

With reference to Background FIG. C, continued capillary sprout growth is dependent upon several processes: the stimulus for growth (angiogenic factors, hypoxia, etc.) must be maintained; the endothelial cells must secrete the proteases required to break down the adjacent tissue; the cells themselves must be capable of movement/migration; and endothelial cell division must take place to provide the necessary number of cells (this takes place at a site behind the growth front of the sprout). Neighboring blind-ended sprouts then join together to form a capillary loop which later matures into a vessel like the one from which it arose.

The list of angiogenesis dependent diseases includes, but is not limited to the following: Angiofibroma which is an abnormal formation of blood vessels which are prone to bleeding; Neovascular Glaucoma which is an abnormal growth of blood vessels in the eye; Arteriovenous malformations which is an abnormal communication between arteries and veins; Nonunion fractures which are fractures that will not heal; Lupus, and other Connective Tissue Disorders; Osler-Weber syndrome which is a genetic condition resulting in abnormal blood vessels which are prone to bleeding; Atherosclerotic plaques which is a hardening of the arteries; Psoriasis which is a common chronic skin condition; Corneal graft neovascularization which is a complication of corneal replacement surgery; Pyogenic granuloma which is a common skin lesion composed of blood vessels; Delayed wound healing; Diabetic retinopathy which is a leading cause of blindness in diabetics; Scleroderma which is a form of connective tissue disease; Granulations (burns); Neoplasm which is an abnormal cell growth forming solid tumors; Hemangioma which is a tumor composed of blood vessels; Trachoma which is a leading cause of blindness in some countries; Hypertrophic Scars which is abnormal scar formation; Retrolental fibroplasia which is abnormal growth of blood vessels in the retina; Hemophilic joints which is bleeding joints; Vascular adhesions which is excessive scarring; osteoarthritis and rheumatoid arthritis; macular degeneration; and pain.

Magnetism is a property of charge in motion and is related to electrical theory. For convenience the terms "non-particle" and "non-photonic" as they are used herein shall refer to a non-particle and non-photon interaction between the field and the target respectively. As set forth in the examples, the target is mammalian tissue. Thus, the field produced by the inventive apparatus and utilized to practice the method of the present invention which has resulted in the inventive discovery disclosed generally and specifically herein could be described as a non-particle phenomenon or non-particle flux field, because of the existence of the two identifiable but distinct constituent components (i.e., magnetism and electricity) and their intimate relationship with one another.

Each individual atom of magnetic substance is, in effect, a tiny magnet with a north pole and a south pole. Magnetic properties of materials may be classified as diamagnetic, paramagnetic, and ferromagnetic. Their classification relates to the manner in which the material reacts in a magnetic field. It is a familiar observation that certain solids such as iron are strongly attracted to magnets, and such materials are called ferromagnetic. Magnetism is also related to current flowing in a conductor. A magnetic field surrounds a conductor through which current travels according to the well known "right hand rule". It is also known that a magnetic field of flux can induce current flow in circuits.

Until now, a method for affecting angiogenesis in biological subjects, particularly mammals, was previously unknown and had not been discovered or invented.

Until now apparatuses and devices which are capable of producing non-particle, non-photon (e.g., x-rays, etc.) fields or fluxes for the purpose of affecting angiogenesis in biological subjects, particularly mammals, was previously unknown and had not been discovered or invented.

SUMMARY OF THE INVENTION

An embodiment of the present invention is directed to a device for establishing or otherwise creating a substantially contained field having magnetic and electric components. An alternate embodiment of such a device includes "three phase" capability.

A magnetic field produced by a permanent magnet source can be said to constitute a first phase. A magnetic field produced solely by a current carrying coil can be said to constitute a second phase. A magnetic field created from a current carrying wire wrapped in conjunction with the magnetic field associated with the permanent magnetic source can be said to constitute a third phase. The third phase can be further described as "additive" or "opposing".

Additive means the direction of the field lines for the permanent magnetic field source and the current carrying coil source are similarly oriented in direction. Opposing refers to the situation where the aforementioned field lines are in opposing direction.

It is important to point out that a device having a single phase capability comprising any or all of the aforementioned first, second or third phase capabilities also comprises the present inventive discovery. That is, the inventive discovery and embodiments of the apparatus portion of the present invention may include the following in combination or isolation: (1) permanent magnets (2) a current carrying wire for producing a magnetic field around it where the lines of magnetic flux are clockwise or counterclockwise around the wire when viewed from a hypothetical common cross-sectional face.

The preferred embodiments of the present invention were found useful for affecting angiogenesis. One of the preferred embodiments is a plurality of permanent magnets oriented in a side by side pole parallel relationship such that the longitudinal axis and poles of a first magnet is placed adjacent to and parallel with the longitudinal axis of an adjacent or second magnet of similar but not necessarily identical configuration or properties.

Yet another of the embodiments includes a coil of conductor such as wire with a voltage drop across its opposing ends wherein the affect of angiogenesis is believed most prominent within the confines of the coil.

An embodiment of the apparatus portion of the present discovery and invention includes a plurality of permanent magnets which are positioned about the periphery of a geometric frame in the form of a circle, rectangle, square or other shape, such as the preferred ellipse having a central opening. Of course, it is also possible that other geometric shapes such as, for example only, half circles, straight segments, etc., may also be used to provide similar or superior results which are unknown at this time.

Placing the magnets in their respective positions, north to north, and south to south, respectively in a side by side parallel relationship, causes the lines of magnetic flux to be distorted from their normal pattern which is present when the magnetic flux of each magnet is studied in isolation and not in the presence of any other. This is due primarily to the inability of magnetic field lines of flux to "overlap" one another, rather they repel one another to occupy a path of least resistance but maintain their individual strength for the most part. In vector analysis, the "length" designating the magnitude of the flux line remains unchanged but its "orientation" or direction will change in the presence of other forces such as adjacent lines of magnetic flux. Thus, the respective elliptical fields for each magnet stretch in the plane of their polar alignment. The existence of a magnetic field attributable to the presence of the magnets establishes the background magnetic field believed useful in contributing to the invention's ability to affect angiogenesis.

The three phase embodiment of the inventive apparatus includes a tightly wound coil of wire wrapped about the plurality of magnets in a direction normal to their longitudinal axis. A current is passed through the coil in one of two directions (e.g., +"additive" or −"opposing" of the aforedescribed third phase). The coil provides a source of magnetic flux, which depending upon the direction of the current flow, supplements or opposes the natural direction of the lines of magnetic flux of the magnetic field produced by the natural magnetic sources. The preferred number of coil wire turns may vary but is believed to be optimal from between two hundred (200) and eight hundred (800) turns. Insulated copper wire is preferred, because of the heat generated in the coil due to the inherent resistance of the wire to carry a current.

Within the coil assembly are a plurality of optional thermal sensors, either resistance or thermocouple type, which measure and indicate the coil temperature at various points. The thermal sensors enable the operator to monitor the potential decay of the magnets which may be weakened by the generated heat of the device depending upon their composition.

The preferred power supply incorporates a transformer capable of delivering up to the preferred amperage range of 0–15 amps of current, the corresponding voltage for which would depend upon the number of turns of wire used to form the coil.

The voltage difference applied to the coil is passed through a voltage regulating device preferably in the nature of a full-wave rectifier set. By passing the output of the rectifier through a double pole double throw ("DPDT") switch assembly, or other suitable switch assembly, the operator may regulate the applied current, and thus the combine generated field, can be changed at will by the operator. The rectifier converts the applied alternating current to a direct current (DC) with a resulting ripple frequency of 120 pulses per second. The nature of the wave form is best described as a one half sine wave or corresponding square wave formation. Both of them can be described as a one half(½) sine or square wave respectively, because the portion of the wave below the base line dividing the wave form is inverted upward above thereby resulting in the 120 pulses a second.

Of course, the 120 pulses a second presumes a 60 cycle supply voltage common in the United States, but may also be a 50 cycle supply voltage which is common in Europe thereby giving rise to 100 pulses per second frequency or other supply voltage that proves useful. In fact, it is believed by some that frequency modulation will enhance the beneficial results of the inventive method and apparatus.

In the preferred embodiment of the apparatus portion of the invention at least one magnet is removed from the plurality of magnetic sources to create a gap in the preferred elliptical string thereof. Physically leaving out magnets during the assembly process and replacing them with non-magnetic material or simply forming an air space therebetween insures that the magnets themselves do not become current carrying conductor and destroy or unnecessarily affect their integrity during operation of the device.

Another preferred embodiment of the invention comprises a coil of wire like that discussed above and substantially identical to the preferred embodiment but for the elimination or removal of the permanent magnets.

The inventions may be summarized in a variety of ways, one of which is the following: a method of affecting angiogenesis in a biological subject comprising the steps of: providing a magnetic field generating device having a frame, producing a magnetic field; and placing a biological subject in the magnetic field and exposing the biological subject to the field.

The inventions may also be summarized as follows: a method of affecting angiogenesis in a biological subject comprising the steps of: providing a magnetic field generating device having a frame, a plurality of magnets capable of producing a magnetic field wherein each of the plurality of magnets has a north pole and a south pole and a longitudinal axis passing therethrough, the plurality of magnets being positioned in a side by side axis parallel orientation and are partially held in place by the frame, a coil of electrically conducting material wrapped about the plurality of magnets and orthogonal to the longitudinal axis of each of the plurality of magnets, and a source of electrical energy for supplying an electrical current to the coil enabling a magnetic field to be produced therefrom; producing a magnetic field by energizing the device to produce a magnetic field in addition to the background magnetic field associated with the plurality of magnets; and placing a biological subject in the combined magnetic field and exposing the biological subject to the field.

The inventions may also be summarized as follows: a method of affecting angiogenesis in a biological subject comprising the steps of: providing a magnetic field generating device having a frame, a coil of electrically conducting material wrapped about the frame, and a source of electrical energy for supplying an electrical current to the coil enabling a magnetic field to be produced therefrom; producing a magnetic field surrounding the coil; placing a biological subject in the magnetic field and exposing the biological subject to the field.

The preferred summarized inventive method also includes providing a combined magnetic field generating device having between 200 and 800 turns of wire; applying an electrical current to the wire in the range of more than 1 amp and less than 15 amps; energizing the coil with an electrical current in the amperage range greater than 1 amp and less than 15 amps; and, exposing the biological subject to the resultant magnetic field produced therefrom. The known preferred amperage range is from between approximately 5 amps and 10 amps, but other ranges are certainly contemplated and considered to be within the scope of the present discovery and invention.

The present invention may also be summarized as follows: an apparatus for affecting angiogenesis in biological subjects, comprising: means for producing a magnetic field, wherein the means includes: a frame, a coil of electrically conducting material wrapped about the plurality of magnets and orthogonal to the longitudinal axis of each of the plurality of magnets; and a source of electrical energy for supplying an electrical current to establish a magnetic field emanating therefrom.

The summary of the preferred inventive apparatus for affecting angiogenesis includes: a switch to enable the electrical current to flow in a first direction and a second direction opposite to the first direction. In one of the embodiments where permanent magnets are present, the plurality of magnets that are positioned in a side by side axis parallel orientation are oriented so that the like poles of the plurality of magnets are positioned adjacent each other. The plurality of magnets that are positioned in a side by side axis parallel orientation are oriented so that the like poles of a majority of the plurality of magnets are positioned adjacent each other; and the frame is substantially elliptical.

A coil of electrically conducting material wrapped about the plurality of magnets and orthogonal to the longitudinal axis of each of the plurality of magnets, further comprises: a plurality of coils. A cover is removably attached to the frame to shield the coil; wherein the cover may be a cooperating cover and frame sized to establish a passage between the coil and the cover to form at least one duct to enable gaseous flow into and out of the passage from a location outside of the passage.

The preferred device for affecting angiogenesis includes a switch which is a double pole double throw switch or a single pole switch whose function is to regulate the current. The plurality of magnets preferably form a continuous uninterrupted belt of magnets; and have at least one gap in the belt.

It is an object of the present invention to provide a device and method for affecting angiogenic activity.

It is an object of the present invention to provide a device and associated method for affecting angiogenesis.

It is an object of the present invention to provide a device and method capable of affecting angiogenic related conditions.

It is an object of the present invention to provide a device and method for slowing or inhibiting the rate of angiogenesis.

It is an object of the present invention to provide an electrical device and method for affecting angiogenic activity.

It is an object of the present invention to provide an electrical device and associated method for affecting angiogenesis.

It is an object of the present invention to provide an electrical device and method capable of affecting angiogenic related conditions.

It is an object of the present invention to provide an electrical device and method for slowing or inhibiting the rate of angiogenesis.

These and other object, features, and advantages of the present invention shall become apparent after consideration of the inventive discovery disclosure provided herein, including the specification, drawings, and claims. All such objects, features and advantages are believed to be within the scope of the present invention even though not specifically set forth in this document.

BRIEF DESCRIPTION OF THE DRAWINGS

FIG. A is a schematic diagram of the cells of a blood carrying vessel;

FIG. B is a schematic diagram similar to that of FIG. A and including information relating to the initiation of angiogenesis;

Figure 8:
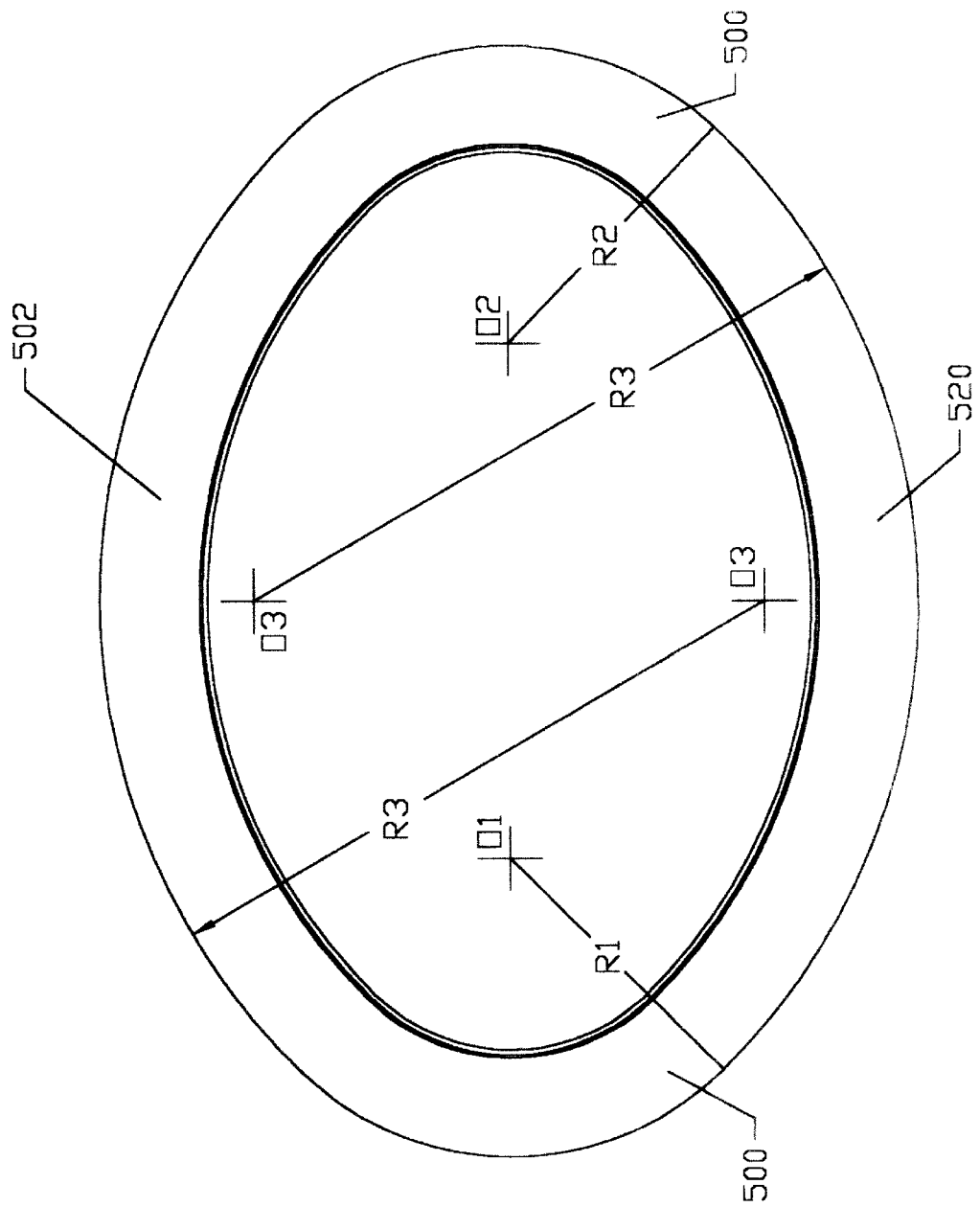
Figure 14:
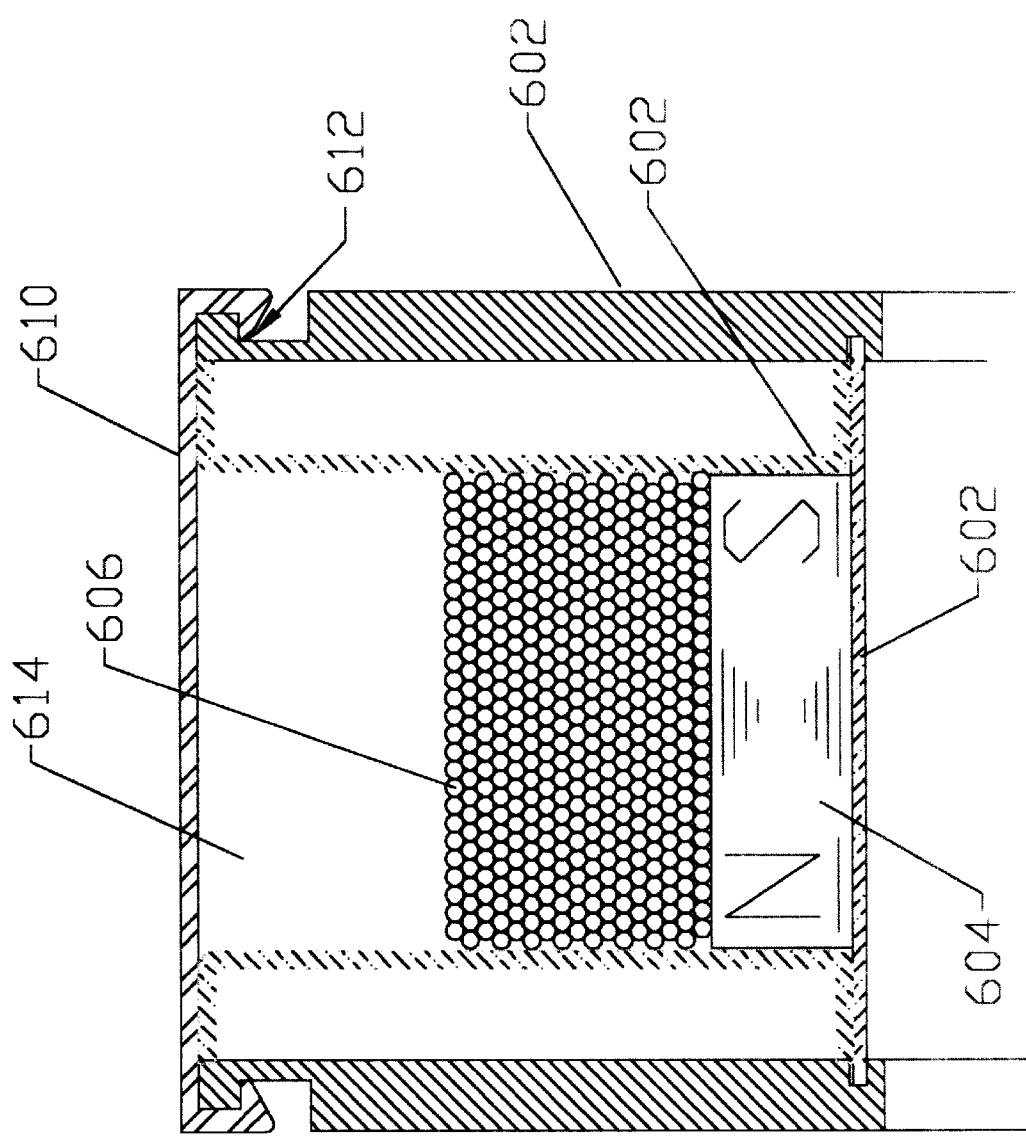
Figure 17:
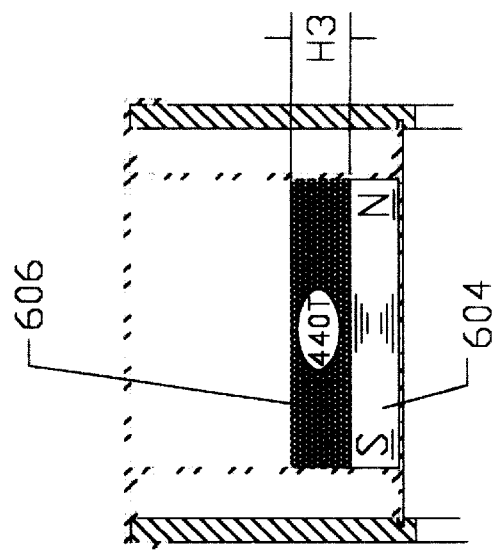
Figure 16:
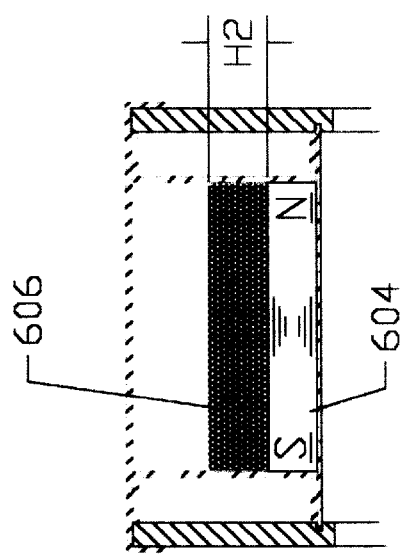
Figure 15:
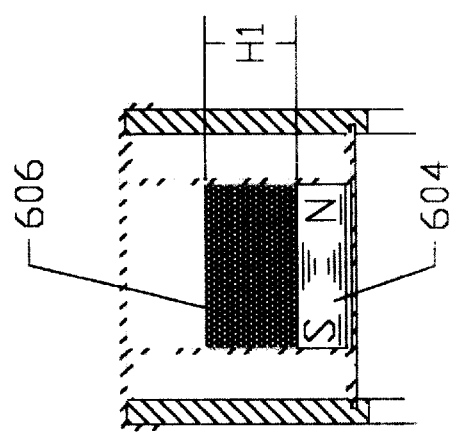
Figure 18:
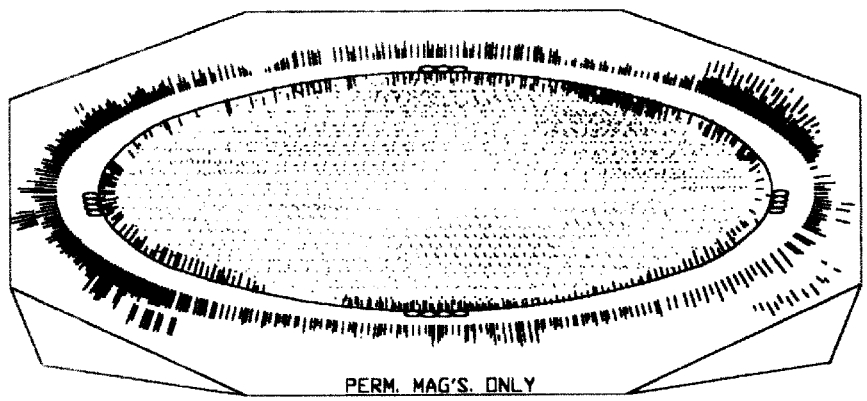
Figure 19:
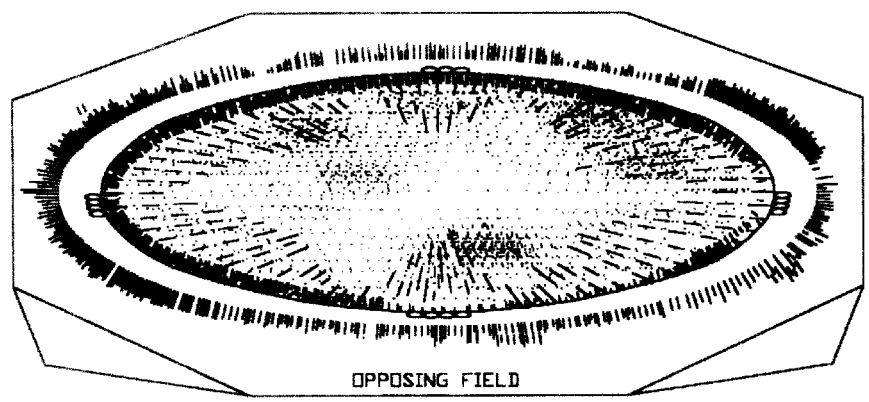
Figure 20:
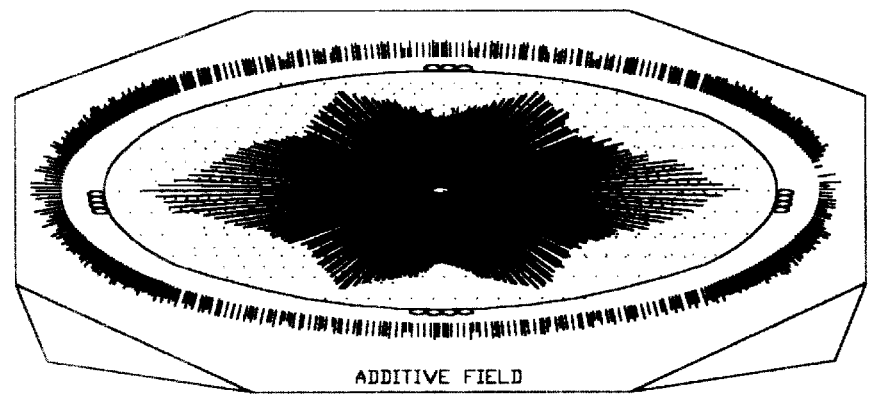

FIG. C is a schematic diagram similar to FIGS. A and B and including information relating to an advanced stage of angiogenesis sometime after the process was initiated;

FIG. 1 is a schematic block diagram of the electrical components of the present invention;

FIGS. 2 and 3 are a front view and back view respectively of an embodiment of an embodiment of a device of the present invention;

FIG. 4 is an end view of the complex magnetic source component shown in FIGS. 2 and 3;

FIGS. 5 and 6 are front and back views of an alternate embodiment of the present invention;

FIG. 7 is an end view of the alternate embodiments of the complex magnetic source component of the present invention shown in FIGS. 5 and 6;

FIG. 8 is a side view of the geometrical construction of an embodiment of the preferred substantially oval or elliptical shape of the present invention which also may take other geometric shapes such as circles, parallelograms, etc.;

FIG. 9 is a front view of an alternate embodiment of the present invention having air flow ducts associated therewith;

FIG. 10 is a top view of the present invention shown in FIG. 9;

FIG. 11 is a side view of the present invention shown in FIG. 9;

FIG. 12 is an illustration of the relative orientation of the magnetic components and coil component of an embodiment of the present invention;

FIG. 13 is a cross-sectional view taken along line A—A of FIG. 12;

FIG. 14 is an enlarged side view of the circled portion of FIG. 13 and further including a cover component;

FIGS. 15–17 are alternate embodiments of the geometry of the present invention shown in FIG. 14 and illustrating a variety of profiles; and FIGS. 18–20 are elevated perspective views of the combined field produced by an embodiment of the combined is field apparatus of the present invention.

DETAILED DESCRIPTION OF THE PREFERRED EMBODIMENT(S)

With reference to the schematic diagram designated as FIG. 1, the power supply designated generally by the reference letter A of that figure and consists of an isolation transformer of suitable capacity. This is attached to a convenient source of commercial power B, is then input into a full wave bridge rectifier C of that figure is of suitable ratings for both voltage and current. The output of this full wave bridge C would then have the characteristics of being a ripple output of direct current characteristics, with the ripple frequency being exactly twice that of the input frequency. This direct current is then output through a switch configuration D, providing a means of conveniently reversing the flow direction of the applied electric energy and the resultant magnetic field from the coil.

With reference to FIGS. 2–8, preferred geometries of the present invention (F in FIG. 1) are illustrated. FIGS. 2–4 show a "small" device designated generally by the reference numeral 300. FIGS. 5–7 show a "large" device designated generally by the reference numeral 400. In each embodiment 300 and 400 of the device as shown in FIGS. 2–7, a central passageway 302 and 402, respectively, is formed inside of the device frame 304 and 404.

As illustrated by the circles 306 and 406, which are of identical size, the relative dimension of the small device 300 is visible with respect to the larger dimension of the larger device 400. With respect to the side or end views of the device (FIGS. 4 and 7), substantially the same geometry is utilized for both devices or the "profile" may be modified in accordance with the teaching set forth herein and below. That is, in one embodiment magnets 308 and 408 are positioned annularly around the surface of the device frame 300 and 400. A coil winding 310 and 410 overlies the annular belt of magnets 408.

With respect to FIG. 8, the substantially oval construction of the device 300 and 400 includes the elements of a geometric ellipse. Origin 1 and origin 2 designated generally by O1 and O2 are the low side of the ellipse. Therefore, O1 and O2 have a designated radii R1 and R2 which sweep through an arc of approximately 90 degree to form the sides of the ellipse. Origin O3 presents a radii R3 to form the top and bottom components of the device. Origin O4 being the centroid of the ellipse also presents a definable radii R4 which is definable for both the top and bottom interior portions of the device. That is, each device consists of end portions 500 as defined by the arc produced by R1 and R2, conjoined with top and bottom portions 502 as defined by the radii O3 or O4 depending upon the frame of reference.

Of course, there are several radii as indicated in the figure but not given reference numerals as they are associated with interior surfaces, magnet layer surfaces as measured at the centroid of the magnet components of the present invention and radii associated with the device in addition to the device frame.

With reference to FIGS. 9–13, an embodiment of the device component of the present invention is designated generally by the reference number 600 in such a manner that the device frame 602 has been partially removed from the device 600 shown in FIG. 12. Specifically, with reference to FIGS. 9, 10 and 11, device 600 is comprised of an annular ring or belt of magnets 604 having a substantially cylindrical configuration and positioned with their poles oriented in a parallel manner such that any two magnets adjacent to one another have aligned north and south poles as indicated by their cylindrical length.

A coil winding 606 overlies the belted or annular layer of magnets 604. With reference to FIGS. 10 and 11, a cover 610 is provided as a means of protecting and shielding the coil 606 during operation. Within the coil assembly are a plurality of optional thermal sensors, either resistance or thermocouple type which measure and indicate the coil temperature at various points. The preferred sensors are manufactured by Honeywell/Microswitch, Inc. and have model number SS94A2. The sensors are used to monitor levels in the coil.

Cover 610 is preferably a section of conventional raceway cover which includes a cooperating tongue and groove snap connection 612 so that the cover may be removed to service the interior magnetic and coil components of the device. As such, the existence of the cover attached to the device frame 602 and the disposition of the magnet and coil establish an air space 614 between the coil 606 and cover 610. The air space 614 provides a means of convective heat transfer such that if an air flow in the air space 614 were induced or created, the flow of air would have a tendency to cool the coil 606 and magnets 604 when they become heated after the coil 606 in energized in the manner described below.

Air ducts 616 are provided to establish a positive air flow within the air space 614. Either air duct 616 may be utilized as the means of ingress or egress depending upon the desired efficiency of the extraction of the heat within the air space 614. That is, air ducts 616 have an interior flow channel 618 to which a supply of forced air (not shown) or other coolant in gaseous form may be introduced and expelled from the air space 614 during operation of the device 600.

With reference to FIGS. 12 and 13, the orientation of the coil 606 and the magnets 604 is readily observed. Cross-section line A–A, which also serves as a vertical axis and horizontal line L, which serves as a horizontal axis, define the centroid of the interior channel 620 of the device. As shown in FIG. 12, there are a pair of gaps 622 in the annular layer or belt of magnets 604. The gaps are provided so as to establish an open circuit condition so that the magnets themselves which are typically made of some metal do not become conductors. They are also believed to provide an oscillating or pulsating (i.e., changing) magnetic field as a function of time.

In either case, current flows through the coil 606 and pursuant to the right-hand rule establishes field lines in either a forward or reverse direction, its additive or subtractive affect with respect to the background magnetic field is interrupted by the gaps 622 in the layer of magnets 604.

With reference to FIGS. 14–17, alternate profiles of the device configuration, namely, the magnet 604 and coil winding 606 orientation with respect to one another is illustrated. For clarity, each small circle 606 is a cross-sectional view of a continuous strand of coil as it is wrapped about the device. Similarly, magnet 604 is substantially cylindrical having ends as shown in FIG. 12 and a length as shown in FIG. 14.

As shown in FIGS. 15–17, the cross-sectional profile of the magnet and coil winding may be modified to several alternate constructions. Focusing solely on the magnet and coil components of the cross-sectional view, it is shown that coil 606 of FIGS. 15–17 may have a varying proportional height H1, H2 and H3, respectively, of FIGS. 15–17. Similarly, magnets 604 may experience a change in dimension but considering the structure of magnets of this type, the strength level of the magnet may simply be varied in accordance with the size.

The magnets shown in FIG. 15 are smaller that those shown in FIG. 16 and FIG. 17; however, in the preferred embodiment of the present invention, the strength of the magnets 604 are identical despite their differing geometry as illustrated in the figures. In such event, each cross-sectional profile shown in FIGS. 15–17 will produce substantially the same characteristics or may exhibit different characteristics depending upon the component selection.

A MODE OF OPERATION

The operation of the inventive apparatus for affecting angiogenesis can be best described in conjunction with a series of examples with supporting data that are set forth below.

Consideration of the known biological attributes of a healthy body were relied upon as known information for the experiments. All laboratory tests and experiments were performed on laboratory mice with active malignant cancer cells in an independent research laboratory facility and setting for affirmation. The intent of the experiments was to analyze the effectiveness of the inventive apparatus and method whose net intended result was proven to have an affect on the rate of angiogenesis.

The following examples, therefore, set forth representative data obtained from some of the experiments and tests which were all conducted in a confidential, controlled, setting. The procedure used for the mammalian animal tests can best be described as follows:

The device and cooling fan to provide air flow in the air space were connected to a standard 110 V electrical service. The device was allowed to warm up through one ten-minute cycle (either positive or negative direction on current flow through coil component). The input current level was adjusted to ten amps during warm up and adjusted periodically to maintain a steady state ten amperes supply current. The net result, depending upon a positive direction or negative direction of current flow was a magnetic field generated from the coil combined with the background magnetic field associated with the magnets.

After warm up, the first animal subjects (i.e., laboratory mice of defined lineage) were placed onto a shelf within the generated combined field. The operator selected a positive or negative direction of current flow through the coil component, as appropriate. The ten amperes of supply current was verified and adjusted if necessary. Periodic checks were performed to maintain ten amps.

A simple current timer as used at the outlet to cut power at the expiration of ten minutes exposure of the subjects to the combined magnetic field. After ten minutes, the device was designed to automatically shut down. The first group of exposed subjects were then removed, placed back in their respective cages and the exposure was performed again and repeated with the next group until all of the subjects were exposed to either a positive or a negative combined field (depending upon the direction of current flow in the coil component), excepting the control animals which received no exposure to the combined field in any way. Measurements of tumor size and animal handling were conducted in accordance with the research facility protocol.

Attached is the method used for treating a group of grey laboratory mice. Twenty (20) control mice and ten (10) mice in each of the treatment groups (i.e., positive and negative direction of current flow through the coil component). All of the mice were selected from a single lineage as good laboratory and experimental practices dictate. Each mouse was implanted with "16/C mammary adenocarcinoma" which is known to be a fast growing "aggressive" tumor model. The treatment began when the median tumor weights reached 100 mg. The treatments were terminated when the tumors became too large to allow the study to continue due to humane considerations (approximately two weeks of treatment).

At the conclusion of the experiment, the mice were analyzed by preparing cross-sectional tumor slides from 3 mice per cage Group (i.e., 3 control, 3 positive, and 3 negative). For each tumor, the independent researcher examined 5 sites on the slide to quantitate it for CD31 staining—a known standard of cellular staining. The data is reported in EXAMPLE ONE below.

EXAMPLE ONE

1) By t-test,
   Cage Group 1 vs Cage Group 2, p=0.0280
   Cage Group 2 vs Cage Group 3, p=0.0128
   Cage Group 1 vs Cage Group 3, p<0.0001
2) By ANOVA (it only gives data at the 95% confidence level),
   Cage Group 1 vs Cage Group 3 P<0.05
   Cage Group 1 vs Cage Group 2 P<0.05
   Cage Group 2 vs Cage Group 3 P<0.05

Example two is a summary table of the 3 mice (slides) for each cage Group. There was a greater reduction in angiogenesis in cage Group 3 than cage Group 2. However, both were statistically significant from the control group.

EXAMPLE TWO

Micro-vessel Density Assessed by CD31 Immunohistochemistry and Image Analysis

Note: The "Sample" designation provided below determines the cage Group number and mouse identity number within the cage Group. Ex.: "Sample 2–4" means cage Group 2 and mouse number 4.

| Sample | % CD31 + Comparison by Slides | | | | | | |
|---|---|---|---|---|---|---|---|
| | Site 1 | Site 2 | Site 3 | Site 4 | Site 5 | MEAN % | STD. DEV. |
| Cage Group 1-1 | 28.88 | 21.17 | 24.04 | 18.27 | 11.76 | 20.82 | 6.40 |
| Cage Group 1-2 | 30.09 | 18.49 | 11.38 | 19.50 | 18.32 | 19.56 | 6.72 |
| Cage Group 1-8 | 15.27 | 13.39 | 30.01 | 33.18 | 22.01 | 22.77 | 8.74 |
| Cage Group 2-2 | 8.81 | 9.04 | 20.27 | 12.65 | 12.08 | 12.57 | 4.64 |
| Cage Group 2-4 | 11.53 | 12.07 | 16.07 | 21.23 | 15.60 | 15.23 | 4.49 |
| Cage Group 2-5 | 8.59 | 10.08 | 26.53 | 28.30 | 18.50 | 18.40 | 9.08 |
| Cage Group 3-4 | 8.07 | 6.98 | 14.63 | 7.06 | 10.01 | 9.35 | 3.19 |
| Cage Group 3-7 | 8.62 | 21.48 | 9.85 | 4.24 | 10.05 | 10.85 | 6.39 |
| Cage Group 3-10 | 24.28 | 4.69 | 4.62 | 10.41 | 10.68 | 10.94 | 8.02 |

EXAMPLE THREE

| Sample | % CD31 + Comparison by Cage Groups | | | | |
|---|---|---|---|---|---|
| | Slide 1 | Slide 2 | Slide 3 | MEAN % | STD. DEV. |
| Cage Group 1 | 20.82 | 19.56 | 22.77 | 21.05 | 1.62 |
| Cage Group 2 | 12.57 | 15.23 | 18.40 | 15.40 | 2.92 |
| Cage Group 3 | 9.35 | 10.85 | 10.94 | 10.38 | 0.89 |

In yet another animal study the same number of mice were used, with the same median tumor weight to begin treatment. The treatment continued for six weeks. Instead of grey mice, nude mice implanted with A549 lung carcinoma were used. The power input was reduced to 7 amps and the time was expanded to 20 minutes twice a day. The exposures were done as early in the morning as possible and as late in the afternoon as possible. Three extra mice were added in each treatment group in the second study. The extra mice were sacrificed after the median tumor weight had doubled. Their tumor tissue was frozen pending the conclusion of the study.

Yet another study was conducted using variations of a preferred embodiment of the apparatus capable of affecting angiogenesis. The apparatus for this study included a current carrying coil wrapped about a frame support structure and complete with electrical supply connections like that described,

EXAMPLE FOUR

The tumor model used in this example was a 16C mammary adenocarcinoma tumor and CD31 staining was used as in all of the other examples. All of exposures, not including the control group which was not exposed to any field, were for ten minutes in duration and performed once per day. The exposures involving the electromagnetic field from the current carrying coil were generated by a 10 ampere supply current load.

The differences in the mean values among the treatment groups are greater than would be expected by chance; there is a statistically significant difference ($P=2.94E-013$).

| % CD31 + Comparison by Cage Groups | | |
|---|---|---|
| Sample | MEAN % | STD. DEV. |
| Cage Group 1 | 18.7 | 2.92 |
| Cage Group 2 | 17.4 | 3.33 |
| Cage Group 3 | 12.3 | 2.99 |
| Cage Group 4 | 15.8 | 2.80 |

The Cage Group 1 mice constituted the control group mice of the study.

The Cage Group 2 mice were exposed to a field generated by an embodiment of the apparatus configured to produce a 1000 Gauss magnetic field about the periphery of the device which resulted in magnetic field of approximately 8–10 Gauss in interior of the device.

The Cage Group 3 mice were exposed to a field generated by the an embodiment of the apparatus configured to produce an electromagnetic field from a current carrying coil of wire as described above whose electrical loading was 10 amperes.

The Cage Group 4 mice were exposed to a field generated by an embodiment of the apparatus configured to produce a combined natural magnetic and electromagnetic field from a current carrying coil as described and was arranged to function in an opposing manner. That is, the Cage Group 4 mice were exposed to a magnetic field from natural magnets about the periphery of the device where the direction of the field lines were opposing the field lines of the magnetic field generated by the current carrying coil.

What is claimed is:

1. A method of affecting angiogenesis in tumors of biological subjects comprising the steps of:
   providing a magnetic field generating device having a frame defining a central passageway and a coil of wire wrapped about the frame;
   producing a magnetic field from the generating device by energizing the coil with electrical energy; and
   placing a biological subject in the central passageway such that the coil surrounds the biological subject, and exposing the biological subject to the field.

2. The method of claim 1, wherein:
   the method of affecting angiogenesis is a method of inhibiting the rate of angiogenesis in tumor tissue.

3. The method of claim 1, further comprising the step of:
   providing a magnetic field generating device having between 200 and 800 turns of wire.

4. The method of claim 3, further comprising the step of:
   applying an electric current to the wire in the range of more than 1 amp and less than 15 amps.

5. The method step of claim 4, wherein:
   the amperage range is from between 5 amps and 10 amps.

6. The method of claim 1, further comprising the step of:
   energizing the coil with an electrical current in the amperage range greater than 1 amp and less than 15 amps.

7. The method of claim 1, further comprising the step of:
   exposing the biological subject to the combined magnetic field for a period of time greater than 5 minutes.

8. A method of affecting angiogenesis comprising the steps of:
   providing a magnetic field generating device having three phase magnetic field generating capability;
   placing a biological subject in the magnetic field produced by the magnetic field generating device and exposing the biological subject to the magnetic field associated therewith.

9. The method of claim 8, wherein:
   the method of affecting angiogenesis is a method of inhibiting the rate of angiogenesis in tumor tissue.

10. The method of claim 8, further comprising the step of:
    providing a combined magnetic field generating device including a plurality of turns of wire and a plurality of permanent magnets.

11. The method of claim 10, further comprising the step of:
    applying an electrical voltage drop across the ends of the wire.

12. The method of claim 8, further comprising the step of:
    energizing the coil with an electrical current in the amperage range greater than 1 amp and less than 15 amps.

13. The method step of claim 12, wherein:
    the amperage range is from between 5 amps and 10 amps.

14. An apparatus for affecting angiogenesis in tumors of biological subjects, comprising:
    means for producing a magnetic field, wherein the means includes:
      a frame having a central passageway,
      a coil made of electrically conducting material wrapped about the frame and surrounding the central passageway; and
      a source of electrical energy for supplying an electrical current to the conducting material to create a magnetic field therefrom.

15. The device of claim 14, further comprising:
    a cover removably attached to the frame to shield the coil.

16. The device of claim 14, further comprising:
    a switch capable of regulating the current flow through the wire.

17. The apparatus of claim 14, wherein:
    the apparatus for affecting angiogenesis is an apparatus for inhibiting the rate of angiogenesis in tumor tissue.

18. The apparatus for affecting angiogenesis of claim 14, further including:
    a substantially elliptical frame.

19. The device of claim 14, such that the coil of electrically conducting material wrapped about the frame, further comprises:

a plurality of coils.

20. The device of claim 14, such that the coil of electrically conducting material wrapped about the frame, further comprises:

at least one coil having between 200 and 800 turns of wire.

21. An apparatus for affecting angiogenesis in tumors of biological subjects, comprising:

means for producing a magnetic field, wherein the means includes:

a frame having a central passageway, a coil made of electrically conducting material wrapped around the frame and the central passageway; and a source of electrical energy for supplying an electrical current to the conducting material to create a magnetic field therefrom; and a plurality of magnets positioned adjacent the coil and constrained from movement by the frame, wherein each of the plurality of magnets has a north pole and a south pole and a longitudinal axis passing therethrough, the plurality of magnets are positioned in a side by side axis parallel orientation and are partially held in place by the frame.

22. The device of claim 21, such that:

the plurality of magnets that are positioned in a side by side axis parallel orientation are oriented so that the like poles of the plurality of magnets are positioned adjacent each other.

23. The device of claim 21, such that:

the plurality of magnets that are positioned in a side by side axis parallel orientation are oriented so that the like poles of a majority of the plurality of magnets are positioned adjacent each other.

24. The device of claim 21, further comprising:

a substantially elliptical frame.

25. The device of claim 21, such that the coil of electrically conducting material wrapped about the frame, further comprises:

a plurality of coils.

26. The device of claim 21, such that:

the plurality of magnets form a belt of magnets having at least one gap in the belt.

27. The apparatus for affecting angiogenesis of claim 21, wherein:

the means for producing a magnetic field is configured to produce a magnetic field useful for inhibiting angiogenesis.

28. A method of inhibiting angiogenesis in tumors comprising the steps of:

providing a magnetic field generating device having a central passageway configured to create a tumor angiogenesis inhibiting magnetic field generating capability;

placing a biological subject in the tumor angiogenesis inhibiting magnetic field and exposing the biological subject to the field.

29. The method of claim 28, further comprising the step of:

providing a magnetic field generating device configured to include a frame having a central passageway and a plurality of turns of wire wrapped about the frame to create an angiogenesis inhibiting magnetic field.

30. The method of claim 29, further comprising the step of:

applying an electrical voltage drop across the ends of the wire.

31. The method of claim 30, further comprising the step of:

energizing the wire with an electrical current in the amperage range greater than 1 amp and less than 15 amps.

32. The method step of claim 31, wherein:

the amperage range is from between 5 amps and 10 amps.

33. A method of inhibiting tumor angiogenesis in a biological subject comprising the steps of:

providing a means for producing an angiogenesis inhibiting magnetic field wherein the means includes a frame and a coil of wire wrapped about the frame;

producing an angiogenesis inhibiting magnetic field by energizing the coil with electrical energy;

exposing a biological subject to the angiogenesis inhibiting magnetic field.

34. The method of claim 33, further comprising the step of:

energizing the coil with an electrical current in the amperage range greater than 1 amp and less than 15 amps.

35. The method step of claim 34, wherein:

the amperage range is from 5 amps to 10 amps.

36. The method of claim 33, further comprising the step of:

exposing the biological subject to the field for a period of time greater than 5 minutes.

37. An apparatus for affecting angiogenesis in tumors of biological subjects, comprising:

means for producing a magnetic field capable of inhibiting angiogenesis in tumors, wherein the means includes:

a frame having a central passageway;

a coil made of electrically conducting material overlying the central passageway; and a source of electrical energy for supplying an electrical current to the conducting material to create a magnetic field therefrom.

38. The device of claim 37, further comprising:

a substantially elliptical frame.

39. The device of claim 37, such that the coil of electrically conducting material wrapped about the frame, further comprises:

a plurality of coils.

40. The device of claim 39, such that the plurality of coils further comprises:

at least one coil having between 200 and 800 turns of wire.

41. The device of claim 37, such that the coil of electrically conducting material wrapped about the frame, further comprises:

a coil having between 200 and 800 turns of wire.

42. The device of claim 37, wherein the frame further comprises:

a central passageway.

43. An apparatus for affecting angiogenesis in tumors of biological subjects, comprising:

means for producing a magnetic field capable of inhibiting angiogenesis in tumors, wherein the means includes:

a frame having a central passageway, a coil made of electrically conducting material wrapped about the frame; and a source of electrical energy for supplying an electrical current to the coil of conducting material which is wrapped around the central passageway enabling an angiogenesis inhibiting magnetic field to be created.

44. The device of claim 43, further comprising:

a substantially elliptical frame.

45. The device of claim 43, such that the coil of electrically conducting material wrapped about the frame, further comprises:

a plurality of coils.

46. The device of claim 45, such that the plurality of coils, further comprises:

at least one coil having between 200 and 800 turns of wire.

47. The device of claim 43, such that the coil of electrically conducting material wrapped about the frame, further comprises:

a coil having between 200 and 800 turns of wire.

48. The device of claim 43, further comprising:

a plurality of magnets positioned adjacent the coil and constrained from movement by the frame.

49. The device of claim 48, wherein:

each of the plurality of magnets has a north pole and a south pole and a longitudinal axis passing therethrough, and the plurality of magnets are positioned in a side by side axis parallel orientation and are partially held in place by the frame.

* * * * *